(12) United States Patent
Kailasam et al.

(10) Patent No.: US 11,244,764 B2
(45) Date of Patent: Feb. 8, 2022

(54) MONITORING PREDICTIVE MODELS

(71) Applicant: CERNER INNOVATION, INC., Kansas City, KS (US)

(72) Inventors: Kanakasabha Kailasam, Olathe, KS (US); Sasanka Are, Kansas City, MO (US)

(73) Assignee: CERNER INNOVATION, INC., Kansas City, KS (US)

( * ) Notice: Subject to any disclaimer, the term of this patent is extended or adjusted under 35 U.S.C. 154(b) by 859 days.

(21) Appl. No.: 15/386,906

(22) Filed: Dec. 21, 2016

(65) Prior Publication Data

US 2018/0173854 A1 Jun. 21, 2018

(51) Int. Cl.
*G16H 50/50* (2018.01)
*G16H 50/70* (2018.01)
*G16H 50/20* (2018.01)

(52) U.S. Cl.
CPC ............ *G16H 50/50* (2018.01); *G16H 50/20* (2018.01); *G16H 50/70* (2018.01)

(58) Field of Classification Search
None
See application file for complete search history.

(56) References Cited

U.S. PATENT DOCUMENTS

| 2008/0147441 | A1* | 6/2008 | Kil | G06Q 50/24 705/2 |
| 2009/0012716 | A1* | 1/2009 | Urdea | G01N 33/48714 702/19 |
| 2009/0299767 | A1* | 12/2009 | Michon | G06Q 50/24 705/3 |
| 2010/0169119 | A1* | 7/2010 | Hussain | G16H 40/20 705/3 |
| 2011/0166883 | A1* | 7/2011 | Palmer | G06Q 50/24 705/3 |
| 2012/0046965 | A1* | 2/2012 | Ryan | G16H 50/30 705/2 |
| 2013/0006130 | A1* | 1/2013 | Oide | A61M 1/3661 600/504 |
| 2013/0132323 | A1* | 5/2013 | Soto | G06Q 50/24 706/47 |
| 2013/0262357 | A1* | 10/2013 | Amarasingham | G16H 50/70 706/21 |
| 2014/0017227 | A1* | 1/2014 | Chew | G16B 40/00 424/130.1 |

(Continued)

*Primary Examiner* — Michael Tomaszewski
*Assistant Examiner* — Jay M. Patel
(74) *Attorney, Agent, or Firm* — Shook Hardy & Bacon LLP

(57) ABSTRACT

Methods, systems, and computer-readable media for a system and method are provided for assessing the value of predictive models monitoring medical conditions. Trends in an individual's medical condition are determined based on monitoring values, and the trends are associated with the actions performed in response to the monitoring values and in accordance with the predictive models. The trends may indicate that an individual's condition is improving, worsening, or remaining stable in response to the action taken. Models used for multiple conditions for an individual or for a population of individuals may be assessed in this manner to generate knowledge regarding the performance of the models based on the actions taken. This knowledge may be used to assess the value of the models in terms of the models' performance and may provide insight on way to improve the models.

19 Claims, 9 Drawing Sheets

(56) References Cited

U.S. PATENT DOCUMENTS

| | | | |
|---|---|---|---|
| 2014/0074510 A1* | 3/2014 | McClung | G16H 50/30 705/3 |
| 2014/0114674 A1* | 4/2014 | Krughoff | G06Q 30/0629 705/2 |
| 2014/0236630 A1* | 8/2014 | Murata | G06Q 10/06398 705/3 |
| 2014/0257122 A1* | 9/2014 | Ong | A61B 5/0468 600/515 |
| 2014/0316813 A1* | 10/2014 | Bauer | G16H 15/00 705/3 |
| 2014/0372138 A1* | 12/2014 | Chari | G16Z 99/00 705/2 |
| 2015/0193583 A1* | 7/2015 | McNair | G16H 50/20 705/2 |
| 2015/0227710 A1* | 8/2015 | Pappada | G06Q 50/22 705/2 |
| 2016/0024583 A1* | 1/2016 | Whitney | G16B 40/00 506/9 |
| 2016/0055589 A1* | 2/2016 | Billings | G06Q 40/08 705/4 |
| 2016/0078183 A1* | 3/2016 | Trygstad | G16H 50/20 706/11 |
| 2016/0106339 A1* | 4/2016 | Behzadi | A61B 5/7275 600/302 |
| 2016/0130656 A1* | 5/2016 | Whitney | C12Q 1/6886 506/9 |
| 2016/0180040 A1* | 6/2016 | Ryan | G06F 3/0685 706/52 |
| 2016/0253687 A1* | 9/2016 | Wei | G16H 40/67 705/3 |
| 2016/0354039 A1* | 12/2016 | Soto | G06Q 40/08 |
| 2016/0364541 A1* | 12/2016 | Flippen | G16H 10/60 |
| 2017/0091391 A1* | 3/2017 | LePendu | G06F 40/279 |
| 2017/0154162 A1* | 6/2017 | Balasubramanian | G16H 20/17 |
| 2018/0286508 A1* | 10/2018 | Leontovich | G01N 33/6869 |

* cited by examiner

MONITORING PREDICTIVE MODELS

BACKGROUND

Many medical systems utilize predictive models to monitor medical conditions and other aspects of the patient care process. These models have sets of suggestions, such as recommended medications or procedures, that are outputted for a particular patient based on received information relating to the patient with the goal of helping clinical decision making and improving the care process. Traditionally, the performance of these models is evaluated only at a macro level. For instance, with a model used to make patient admission faster, the number of admissions before the model and the number of admissions when using of the model may be considered to determine whether the model is generating output that is effectively improving the admission process. This traditional method for assessing a predictive model does not, however, provide insight on each of the output options with respect to performance or knowledge on how to improve the model, nor does it take into account whether and when the model's recommended course of action was actually taken. Accordingly, assessing the value of a predictive model has been limited.

SUMMARY

This summary is provided to introduce a selection of concepts in a simplified form that are further described below in the detailed description. This summary is not intended to identify key features or essential elements of the claimed subject matter, nor is it intended to be used in isolation as an aid in determining the scope of the claimed subject matter.

Embodiments described in the present disclosure are directed to providing assessments of or insight into the performance of predictive models used in a medical care setting. In particular, embodiments may determine trends in an individual's medical condition based on monitoring values and associate the trends with actions performed in response to the monitoring values. The trends may indicate that an individual's condition is improving, worsening, or remaining stable in response to the action taken. Models used for monitoring multiple conditions for an individual or for a population of individuals may be assessed in this manner to generate knowledge regarding the performance of the models. This knowledge may be used to assess the value of the models in terms of the models' performance and to improve the models, which may including evaluating recommended actions and a possible need for alternate approaches.

DETAILED DESCRIPTION

Figure 1:
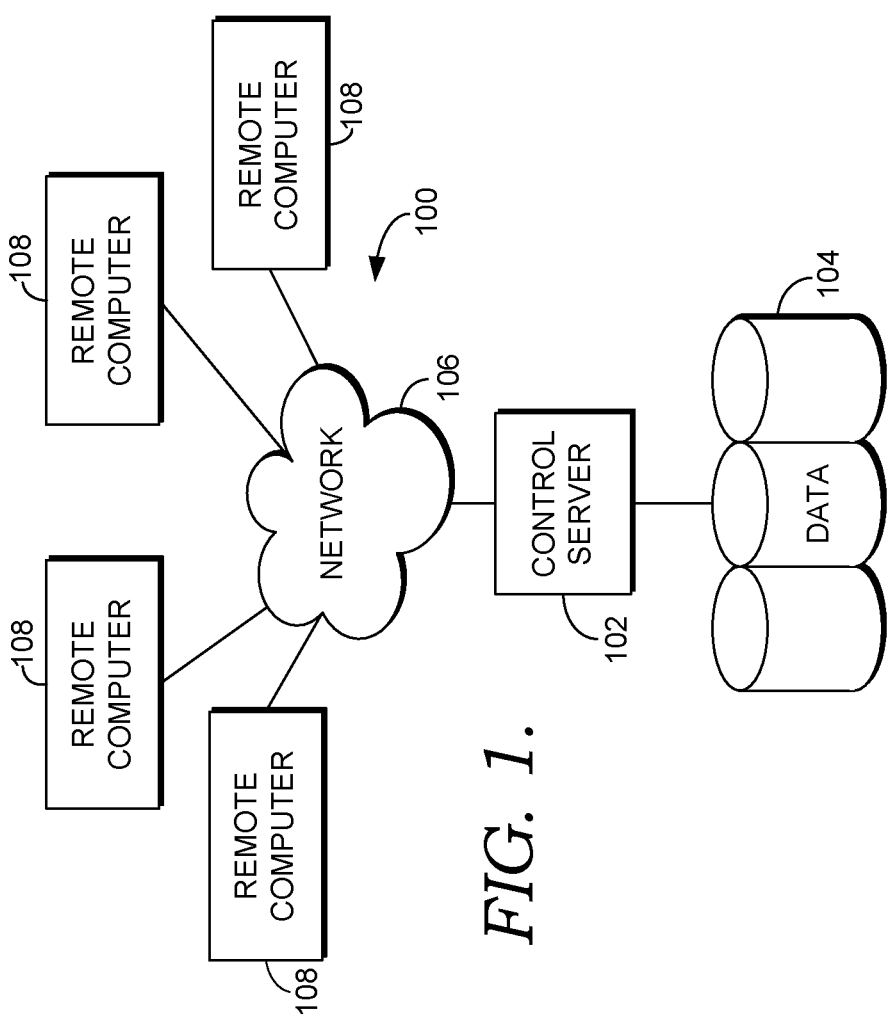
FIG. 1 is a block diagram of an exemplary computing environment suitable to implement embodiments of the present invention.

The subject matter of the present invention is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies. Moreover, although the terms "step" and/or "block" may be used herein to connote different elements of methods employed, the terms should not be interpreted as implying any particular order among or between various steps herein disclosed unless and except when the order of individual steps is explicitly described.

Embodiments described in the present disclosure are directed to assessing the performance of predictive models used for monitoring medical conditions of patients. Predictive models receive input relating to individuals' medical conditions, such as information relating to the individual's vitals or laboratory test results, and generate output designed to improve the medical conditions, such as recommending a medication or procedure. Accordingly, one measure of value of these predictive models is whether the individual's condition is actually improving with the use of the predictive model. Traditional methods for assessing this value have been done a macro level by looking only at the end result for an entire population of patients. For instance, for a model used to increase patient admissions, the number of admissions before prior to using the model is compared to the number of admissions when using the model to determine whether the model is generating output that is effectively improving the patient admission process. Because each model may have several output options (i.e., recommended actions), this approach to determining a model's value overlooks the performance of the model in terms of each output for actions to suggest. Further, because some models recommend actions that a clinician must then decide whether to execute, assessment of a model on a macro level can overlook whether the model's recommended action was the action actually taken and, if an alternate action was taken, whether the alternate action improved the outcome. Accordingly, these approaches are not always accurate. Additionally, while performance assessment of a model measured on a macro level may provide a rough estimation of the models' effectiveness, it does not provide any guidance or insight on how to improve the model.

Embodiments of the disclosed invention overcome these limitations by determining the effectiveness of a model on an individual action level. In particular, embodiments of the present invention are directed to methods, systems, and computer-readable media for a system and method to determine trends in an individual's medical condition based on monitoring values and associate the trends with actions performed in response to the monitoring values and in accordance with the predictive models. The trends may indicate that an individual's condition is improving, worsening, or remaining stable in response to the action taken. Models used for multiple conditions for an individual or for a population of individuals may be assessed in this manner to generate knowledge regarding the performance of the models based on the actions taken. This knowledge may be used to assess the value of the models in terms of the models' performance, including knowledge on a patient-level and/or action level, rather than merely as a population, and may provide insight on how to improve the models. Such improvements may include, among other things, evaluating the effectiveness of recommended actions, including whether the recommendations are being taken and/or whether they result in an improved condition, and considering the need for and effectiveness of alternative actions.

The claimed solution is necessarily rooted in computerized electronic medical record technology to overcome a problem specifically arising in the realm of electronic care decisions technology. Specifically, the effectiveness of models used to implement electronic care decisions technology is a measure of the model's value, but this is often not fully realized under the traditional macro-level approach to valuating a model. If adhering to the routine, conventional function of setting medication reminders, the value of a model may not accurately depict when the recommended action suggested by the model leads to an improvement in the medical condition compared to an action taken that was not recommended. Further, the conventional methods do not generate knowledge on effectiveness of different aspects of the model to improve the model.

An exemplary computing environment suitable for use in implementing embodiments of the present invention is described below. FIG. 1 is an exemplary computing environment (e.g., medical-information computing-system environment) with which embodiments of the present invention may be implemented. The computing environment is illustrated and designated generally as reference numeral 100. The computing environment 100 is merely an example of one suitable computing environment and is not intended to suggest any limitation as to the scope of use or functionality of the invention. Neither should the computing environment 100 be interpreted as having any dependency or requirement relating to any single component or combination of components illustrated therein.

The present invention is a special computing system that can leverage well-known computing system environments or configurations. Examples of well-known computing systems, environments, and/or configurations that might be suitable for use with the present invention include personal computers, server computers, hand-held or laptop devices, multiprocessor systems, microprocessor-based systems, set top boxes, programmable consumer electronics, network PCs, minicomputers, mainframe computers, distributed computing environments that include any of the above-mentioned systems or devices, and the like.

The present invention might be described in the context of computer-executable instructions, such as program modules, being executed by a computer. Exemplary program modules comprise routines, programs, objects, components, and data structures that perform particular tasks or implement particular abstract data types. The present invention might be practiced in distributed computing environments where tasks are performed by remote processing devices that are linked through a communications network. In a distributed computing environment, program modules might be located in association with local and/or remote computer storage media (e.g., memory storage devices).

With continued reference to FIG. 1, the computing environment 100 comprises a computing device in the form of a control server 102. Exemplary components of the control server 102 comprise a processing unit, internal system memory, and a suitable system bus for coupling various system components, including data store 104, with the control server 102. The system bus might be any of several types of bus structures, including a memory bus or memory controller, a peripheral bus, and a local bus, using any of a variety of bus architectures. Exemplary architectures comprise Industry Standard Architecture (ISA) bus, Micro Channel Architecture (MCA) bus, Enhanced ISA (EISA) bus, Video Electronic Standards Association (VESA) local bus, and Peripheral Component Interconnect (PCI) bus, also known as Mezzanine bus.

The control server 102 typically includes therein, or has access to, a variety of non-transitory computer-readable media. Computer-readable media can be any available media that might be accessed by control server 102, and includes volatile and nonvolatile media, as well as, removable and nonremovable media. By way of example, and not limitation, computer-readable media may comprise computer storage media and communication media. Computer storage media includes both volatile and nonvolatile, removable and non-removable media implemented in any method or technology for storage of information such as computer-readable instructions, data structures, program modules or other data. Computer storage media includes, but is not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium which can be used to store the desired information and which can be accessed by control server 102. Communication media typically embodies computer-readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of any of the above should also be included within the scope of computer-readable media.

The control server 102 might operate in a computer network 106 using logical connections to one or more remote computers 108. Remote computers 108 might be located at a variety of locations in a medical or research environment, including clinical laboratories (e.g., molecular diagnostic laboratories), hospitals and other inpatient settings, veterinary environments, ambulatory settings, medical billing and financial offices, hospital administration settings, home healthcare environments, and clinicians' offices. Clinicians may comprise a treating physician or physicians; specialists such as surgeons, radiologists, cardiologists, and oncologists; emergency medical technicians; physicians' assistants; nurse practitioners; nurses; nurses' aides; pharmacists; dieticians; microbiologists; laboratory experts; laboratory technologists; genetic counselors; researchers; veterinarians; students; and the like. The remote computers 108 might also be physically located in nontraditional medical care environments so that the entire healthcare community might be capable of integration on the network.

The remote computers 108 might be personal computers, servers, routers, network PCs, peer devices, other common network nodes, or the like and might comprise some or all of the elements described above in relation to the control server 102. The devices can be personal digital assistants or other like devices.

The computer network 106 may comprise local area networks (LANs) and/or wide area networks (WANs). Such networking environments are commonplace in offices, enterprise-wide computer networks, intranets, and the Internet. When utilized in a WAN networking environment, the control server 102 might comprise a modem or other means for establishing communications over the WAN, such as the Internet. In a networking environment, program modules or portions thereof might be stored in association with the control server 102, the data store 104, or any of the remote computers 108. For example, various application programs may reside on the memory associated with any one or more of the remote computers 108. It will be appreciated by those of ordinary skill in the art that the network connections shown are exemplary and other means of establishing a communications link between the computers (e.g., control server 102 and remote computers 108) might be utilized.

In operation, an organization might enter commands and information into the control server 102 or convey the commands and information to the control server 102 via one or more of the remote computers 108 through input devices, such as a keyboard, a microphone (e.g., voice inputs), a touch screen, a pointing device (commonly referred to as a mouse), a trackball, or a touch pad. Other input devices comprise satellite dishes, scanners, or the like. Commands and information might also be sent directly from a remote healthcare device to the control server 102. In addition to a monitor, the control server 102 and/or remote computers 108 might comprise other peripheral output devices, such as speakers and a printer.

Although many other internal components of the control server 102 and the remote computers 108 are not shown, such components and their interconnection are well known. Accordingly, additional details concerning the internal construction of the control server 102 and the remote computers 108 are not further disclosed herein. Additionally, it should be understood that any number of user devices, servers, and data sources may be employed within computing environment 100 within the scope of the present disclosure. Each may comprise a single device or multiple devices cooperating in a distributed environment. For instance, control server 102 may be provided via multiple devices arranged in a distributed environment that collectively provide the functionality described herein. Additionally, other components not shown may also be included within the distributed environment.

Figure 2:
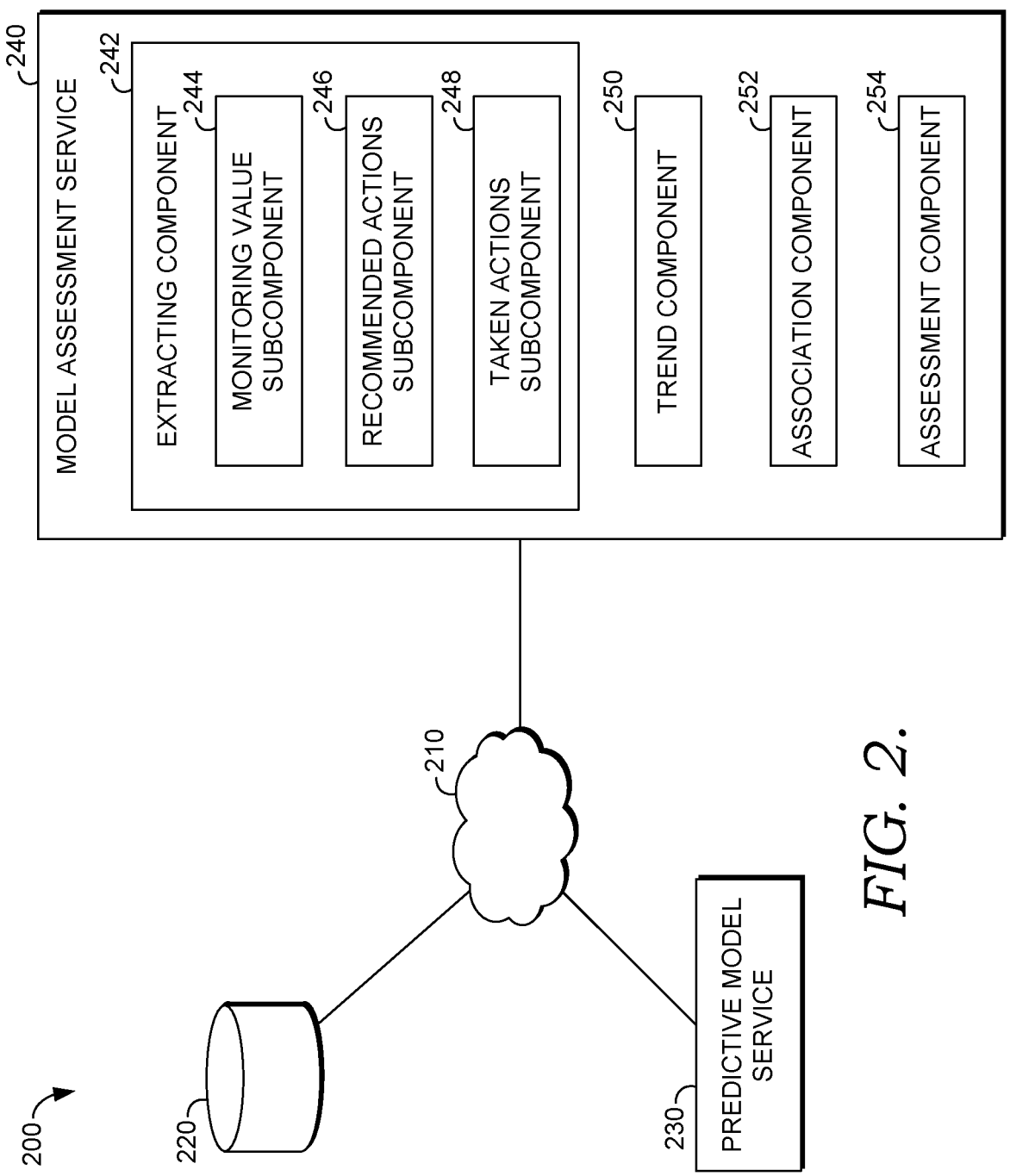
FIG. 2 is an exemplary system architecture suitable to implement embodiments of the present invention.

In an embodiment exhibited by FIG. 2, the processing duties may be split among several computing systems. The data store 220 may be implemented through a database system and may be an electronic medical record (EMR). The network 210, such as the internet or other public or private network, serves as a communications link between the data store 220, one or more predictive model services 230, and one or more model assessment services 240. The tasks performed by the processor utilize a variety of computer technology. Although the embodiment illustrated in FIG. 2 depicts the data store 220, the predictive model service 230, and the model assessment service 240 as being remote and communicatively coupled through the network 210, it is also contemplated herein that the data store 220, predictive model service 230, and the model assessment service 240 may also reside on a single computing device rather than through a distributed architecture.

The predictive model service 230 may perform operations to execute one or more predictive models for an individual or population of individuals. As briefly described above, predictive models may be used to monitor a medical condition of an individual, such as a patient. As used herein, medical condition refers to a disease, diagnosis, medical issue, or medical event for a patient. A medical event may include, for example, an individual's discharge or admittance into a particular department within a medical facility or treatment by a medical professional.

The predictive model service 230 may use input relating to the medical condition, such as physiological information or non-physiological information. Physiological information may relate the functioning of an individual's body such as, for example, heart rate, blood glucose levels, blood pressure, cardiac rhythms, neurological activity, and other vital signs measuring physiological variables. Non-physiological information may relate to the patient care process and include, for example, a time between a discharge order and actual discharge of a patient. In some embodiments, this input is received from the patient's EMR stored in the data store 220. The input may also be received directly from remote monitoring devices.

The predictive model service 230 may use this input to generate output, which may include monitoring values and actions to be taken in response to the monitoring values. Generally, the predictive model service 230 calculates a numerical condition score that is then classified into a pre-defined risk level or category. The condition score and the corresponding risk category may both be considered a monitoring value computed by the predictive model service 230. In exemplary embodiments, a monitoring value characterizes a medical condition with respect to a particular individual. The monitoring value may indicate a risk or likelihood of developing or having a medical condition or indicate a degree of seriousness of an existing medical condition. It is also contemplated that the monitoring value may indicate a time related to a medical condition. For instance, if the medical condition is discharge from the emergency department, the monitoring value may be an amount of time between two events in the discharge process. A monitoring value may be a numerical figure, such as a risk percentage or amount of time, or a qualitative category.

Different predictive models may utilize a different number of monitoring values. For instance, one predictive model may output monitoring values of high risk, high-medium risk, medium risk, medium-low risk, and low risk while another predictive model uses only high risk, medium risk, and low risk. Additionally, the monitoring values based on condition scores may be defined with different parameters based on the predictive model and/or facility using the model. For example, one medical facility may define a high risk level of including condition scores between 100 and 70 while another medical facility may define a high risk level of including only condition scores between 80 and 100.

As previously mentioned, output of the predictive model service 230 may also include recommended actions based a monitoring value, such as a condition score or risk level. Actions may include an event, such as assigning a health coach, ordering a procedure, and placing orders, including prescribing a drug or medication, to initiate risk reduction. In some embodiments, the action may include continued monitoring or an inaction in which no particular action is suggested for the patient. In some embodiments, a medical professional or user is presented with the monitoring value and/or the action and determines whether to perform the recommended action. Accordingly, the action taken may be the recommended action. In some instances where the medical professional disagrees with the recommended action, the action taken may not be the recommended action. For example, the medical professional may suppress or invalidate the predictive model's recommendation for an action. Accordingly, a suppression or invalidation may also be considered an action taken.

Following an action being taken, additional input relating to the medical condition may be received. For example, if an action taken is ordering a procedure for the patient, the predictive model may receive new psychological values after the procedure. A subsequent monitoring value and, in some embodiments, a recommended action may be determined based on the new input. This process of receiving input values, computing monitoring values, recommending actions, and taking actions may continue until the individual is no longer a candidate for monitoring of the medical condition through the predictive model.

The model assessment service 240 may provide an assessment of performance of one or more predictive models being executed by the predictive model service 230. Accordingly, the model assessment service 240 may include an extracting component 242 that extracts or receives information relating to the use of the predictive model, a trend component 250 that determines trends in the information received by the extracting component 242, an association component 252 that associates trends with information received, such as actions suggested or taken, and an assessment component 254 that provides an assessment of a predictive model's performance based on the determined trends.

The extracting component 242 may include one or more subcomponents relating to different information that is extracted. Specifically, some embodiments of the extracting component 242 include a monitoring value subcomponent 244, a recommended action subcomponent 246, and a taken action subcomponent 248. The monitoring value subcomponent 244 may determine monitoring values being generated for individuals for which a predictive model is being used. Monitoring values provide an indication of an individual's medical condition as computed using the predictive models. The monitoring value subcomponent 244 may determine the monitoring values by extracting or receiving this information directly from the predictive model service 230 or from an individual's EMR stored in a remote data store, such as data store 220.

The recommended action subcomponent 246 may determine actions suggested by the predictive model service 230 in response to the monitoring values generated for an individual. A recommended action may include placement of orders, procedures or other events. Similarly, the taken action subcomponent 248 may determine an action actually taken in response to monitoring values. A taken action may include placement of orders, procedures or other events, or may be the suppression or invalidation of a recommendation for an action. The recommended action subcomponent 246 and the taken action subcomponent 248 may determine recommended actions and taken actions by receiving or extracting this information directly from the predictive model service 230 or from the individual's EMR stored in a remote data store, such as data store.

Figure 3:
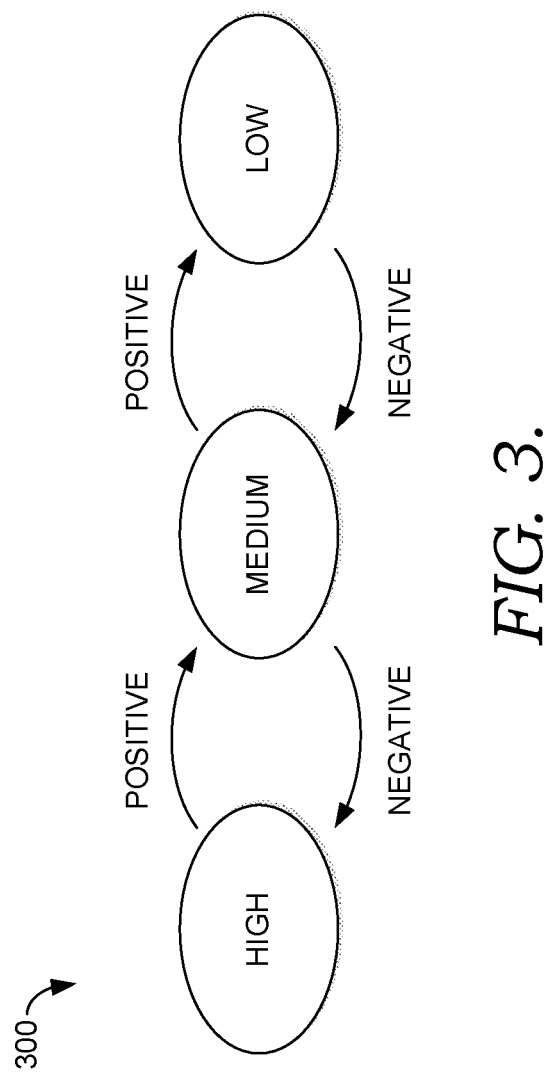
FIG. 3 is a graphical illustration of trends in risk levels determined in accordance with embodiments of the present invention.

In embodiments of the disclosed invention, the trend component 250 of the model assessment service 240 discovers trends in monitoring values based on the determined monitoring values for individuals. A trend in monitoring values indicates a change, if any, in the monitoring values. A trend may be a positive, negative or neutral trend. As used herein, a positive trend may indicate that the medical condition with respect to an individual is improving, such as with a decrease in a risk level for the medical condition, while a negative trend may indicate that the medical condition is worsening, such as with an increase in risk level for the medical condition. A neutral trend may indicate no change or no significant change in the individual's medical condition. Turning briefly to FIG. 3, a visual representation 300 of trends as they related to changes in risk levels is provided. As shown, when the risk level for a patient moves from high to medium and from medium to low, there is a positive trend in monitoring values, and when a patient moves from low to medium and from medium to high, there is a negative trend.

In addition to indicating a type of trend (e.g., positive, negative, neutral), some embodiments of trend component 250 may determine a magnitude of the trend. For example, some trends indicating movement from one risk category to a different risk category immediately adjacent the initial risk category. Trends, however, may also indicate movement spanning multiple trend categories. For instance, if monitoring values for a particular predictive model classify an individual as "high", "medium", and "low" risk, a positive trend may be moving simply from "high" risk to "medium" risk or a positive trend may be moving from "high" risk to "low" risk. The degree of change in risk level is also referred to herein as the magnitude of the trend.

Once trends are discovered, an association component 252 may associate each discovered trend with at least an action taken. The action taken associated with the trend may be an action taken between computation of the monitoring values on which the trend is based. For instance, in response to an individual having a monitoring value of "high" risk, a medication may have been ordered, and a subsequent monitoring value of "medium" risk may have been computed for the individual. The positive trend of moving from high risk to medium risk may be associated with the action of ordering a medication. As another example, in response to an individual having a monitoring value of medium risk, a clinician may have ignored a recommendation to taken an action, and a subsequent monitoring value for the individual may be medium risk. The neutral trend of no movement from medium risk category may be associated with the clinician's ignoring the recommended action. In this way, the trends are associated with actions to indicate the action's possible effect on the medical condition.

In some embodiments, the association component 252 also associates additional information relating to the action with the trend. The association component 252 may associate, for example, a time period between the time the variables are measure for computation of a monitoring value and the time action is taken in response to the monitoring value. In other embodiments, the time period associated with the action may be between the time a recommended action is provided to a clinician and the time an action is actually taken. Additional information that may be associated with a trend includes demographic information about the individual, the individual's medical history, information about the medical facility or department in which the individual was being monitored, and/or any actions recommended by the predictive model that were not taken.

After trends are associated with actions taken and other information relating to the predictive models, the assessment component 254 may analyze the trends and associated actions and other information to assess the performance of the predictive model. The analysis of the trends includes determining whether the medical condition tends to improve, decline, or remain stable based on the actions taken. The assessment component 254 may first determine overall frequencies with which the medical condition for individuals improves, worsens, or remains stable by aggregating the associations between trends and actions for each individual having a common medical condition being monitored by the same predictive model. For example, the assessment component may determine that, for a population of individuals being monitored for diabetes, the risk of diabetes has improved 80% of the time, declined 6% of the time, and remained stable 14% of the time. The assessment component 254 may also determine a frequency with which a medical condition improves, declines, or remains stable based on an action taken. Continuing with the diabetes example, the assessment component may determine that diabetes within the population improved 90% of the time a prescription for metformin was ordered but improved only 60% of the time that the action taken was assigning a health coach. By assessing the performance of predictive models based on each type of action taken, embodiments of the disclosed invention may provide insights on how to improve the predictive models. Further, performance of the predictive models may be assessed based on the initial monitoring value of the individuals. For example, the assessment component 254 may determine that medical condition improved 85% of the time for individuals having an initial or first monitoring value of medium or low risk but that the medical condition improved only 65% of the time for individuals having an initial monitoring value of high risk. In this way, embodiments of the disclosed invention may provide insight as to whether a predictive model is working better for more severe or less severe cases of the medical condition.

As mentioned, the predictive model may provide recommended actions, and a clinician-user takes an action based on the recommendation. Accordingly, embodiments of the assessment component 254 may further determine, based on the trends, whether the medical condition of the individuals tends to improve, decline, or remain stable when the action taken or initiated by the clinician is the recommend action. For instance, the assessment component 254 may determine that, for individuals being monitored for a risk of sepsis, their risk of sepsis improves 66% of the time that the action taken is the action recommended by the predictive model and improves 15% of the time the action taken is not the action recommended. The analysis of the trends in monitoring values using whether the action taken is the recommended action can also be determined based on the type of action.

In some embodiments, the assessment component 254 further provides an assessment of the predictive model based on time periods associated with the trends. A time period may represent an amount of time between the time a first monitoring value for an individual is computed and when the corresponding action is taken in response to the first monitoring value. The time period may be expressed in various units such as minutes, hours, days, and the like. Accordingly, the assessment component 254 may analyze whether the amount of time between a monitoring value and corresponding action affects the trends in the medical condition. For instance, the assessment component 254 may determine individuals given a medication within one hour of the first monitoring value tend to experience a positive trend of moving from high risk to low risk while individuals given the same medication at a time between three and five hours of the first monitoring value tend to experience a trend of moving only from high risk to medium risk. This analysis may indicate the most effective time period for taking an action. Similarly, with this analysis based on timing, embodiments of the present disclosure may be used to determine an expiring period after which a particular action is no longer effective. For example, if the assessment component 254 determines that the frequency of a positive trend occurring dramatically decreases and/or the frequency of a negative trend increases when a procedure is performed after the initial 24 hours following the first monitoring value, it may be determined that the procedure has an expiration period of 24 hours.

Further, in some embodiments, the assessment component 254 may determine typical trajectories for a particular monitoring value for a medical condition. These typical trajectories may indicate an order or sequence for typical actions taken for the medical condition and the expected path of an individual's monitoring values in response to each typical action. For example, it may be determined that individuals at a high risk of a medical condition generally are given a first medication, found to be at a medium risk within 48 hours of the first medication, given a second medication in response to the medium risk monitoring value, and found to be at a low risk within one week of starting the second medication. Typical trajectories may be used as a guideline when tracking the progress of a particular individual. If the individual's path is deviating from the typical trajectory, a medical professional may be alerted as the individual may benefit from further examination or a unique treatment plan.

Although the examples provided have focused on assessment of a single predictive model monitoring a single medical condition, the assessment component 254 may be used to assess multiple predictive models used for individuals at the same or different medical facilities and/or departments. The different predictive models may be used to monitor related or unrelated medical conditions. For example, the assessment component 254 may aggregate the trends associated with actions taken in accordance with a predictive model monitoring diabetes and trends associated with actions taken in accordance with a predictive model monitoring hypertension, which is commonly presented with diabetes. In another example, the assessment component 254 may provide an assessment of the performance of every predictive model used within a particular health care facility, which may provide insight on how the department is utilizing the predictive models.

Figure 4:
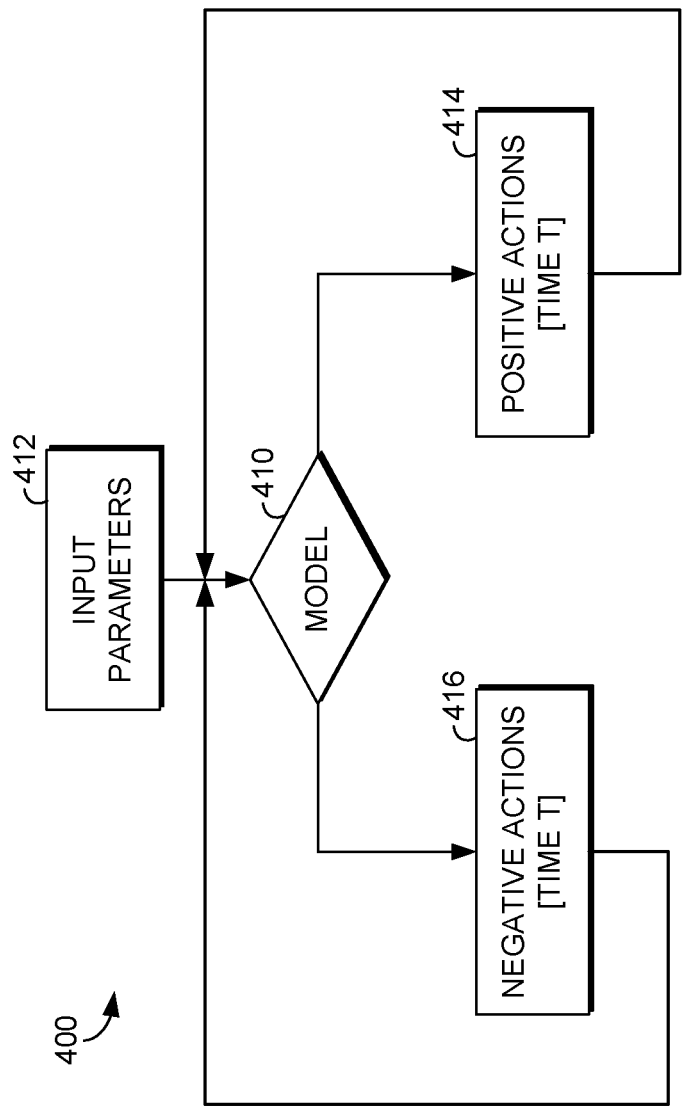
FIG. 4 is a flow diagram of a predictive model providing output for assessment in accordance with embodiments of the present invention.

As previously mentioned, output of the predictive models that is monitored and assessed by the model assessment service 240 may be used to evaluate the performance of a predictive model. Generally, a predictive model may be determined to have a higher value when there are high frequencies of positive trends associated with recommended actions. Additionally, the output of the predictive models may be used as input to improve performance of the predictive model. Turning to FIG. 4, for example, a flow diagram 400 showing a predictive model 410 is provided. Qualification criteria may be set to determine if the predictive model 410 should provide a monitoring value. As illustrated, the qualification criteria may include input parameters 412 for the input received relating to the medical condition as well as the output previously taken, such as the recommended actions 414 and 416. The recommended actions may include positive action 414, which are those associated with positive trends in monitoring values, or a negative action 416, which may actions associated with negative trends in monitoring values. Neutral trends may also be considered and fed back into the model. Times relating to each of the actions may also be used as to determine the qualification criteria. Accordingly, this outcome data may be used to provide insight into the model behavior for both individual and a specific population and may be used to further calibrate the model for a specific population.

Figure 5A:
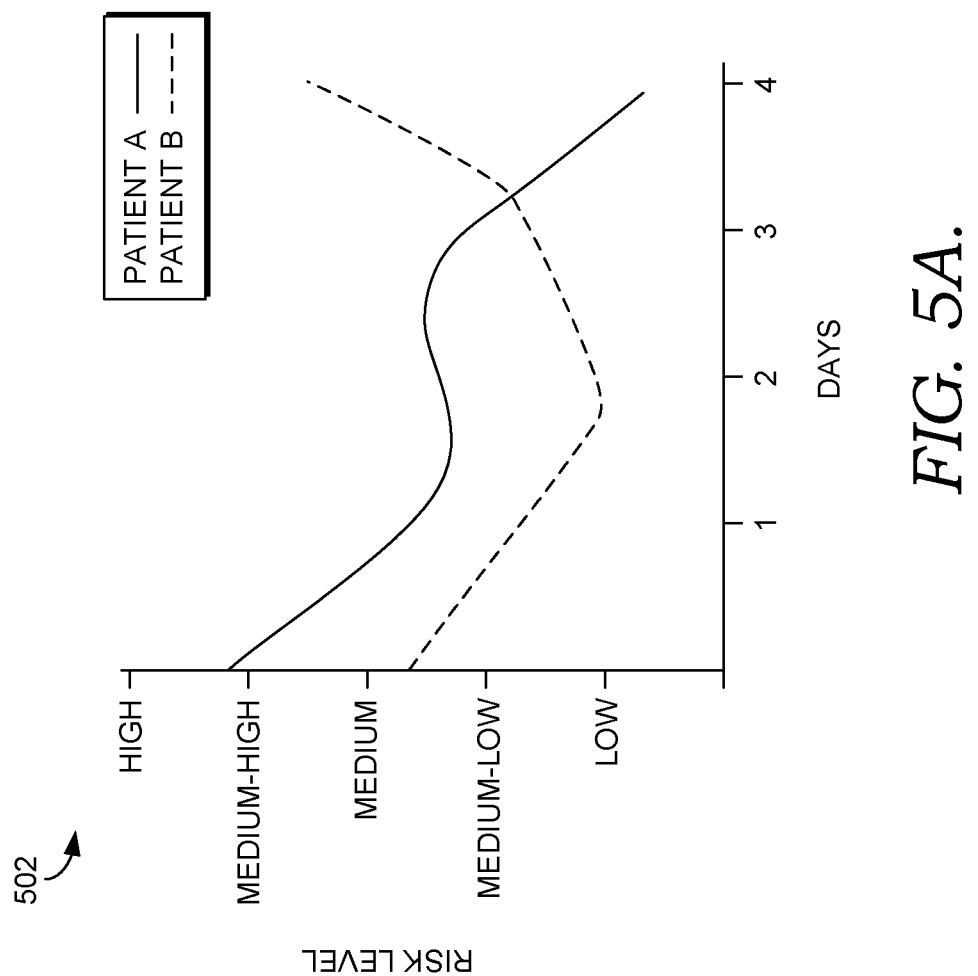
FIGS. 5A-5C are example graphic representations of the performance of a predictive model generated in accordance with embodiments of the present invention.
Figure 5B:
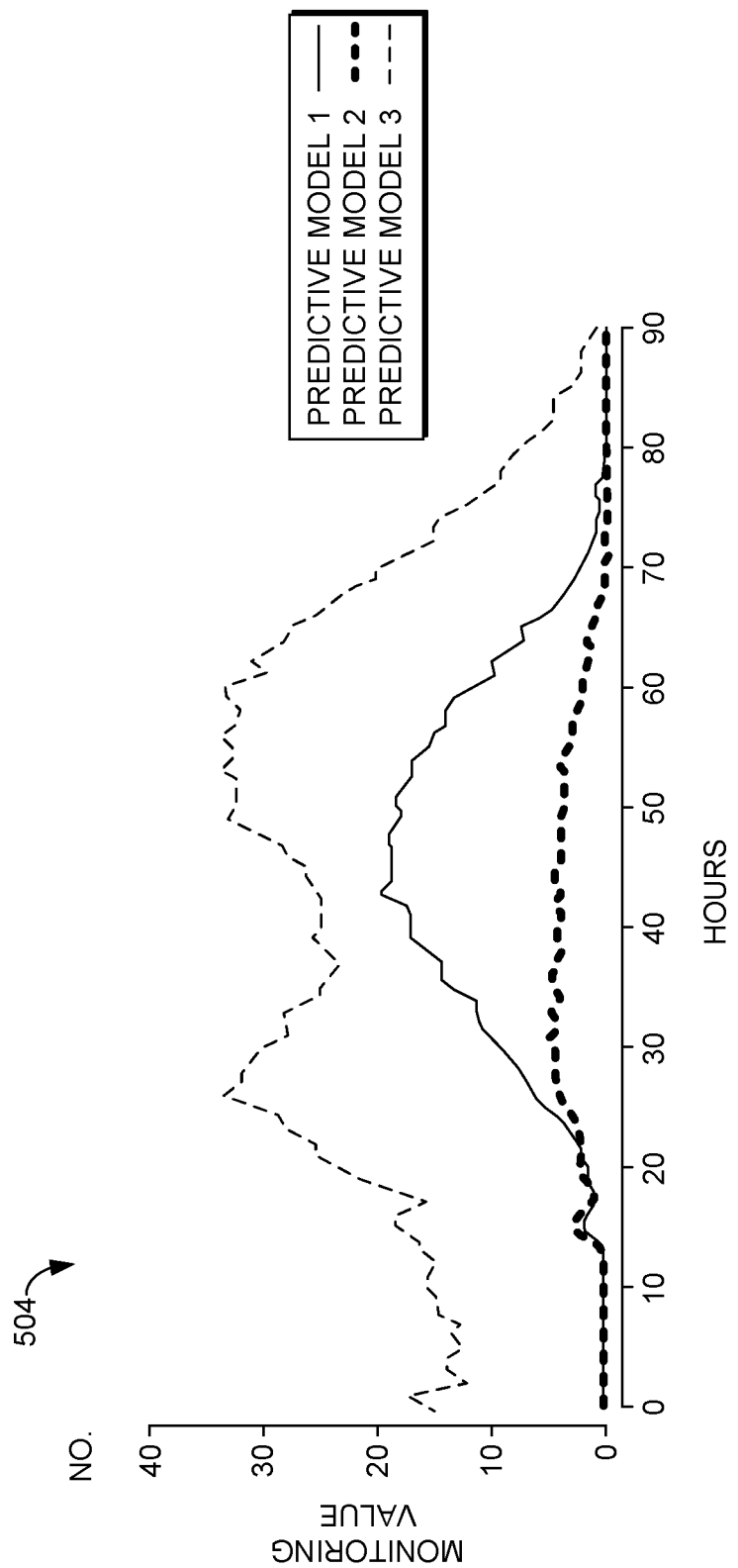
Figure 5C:
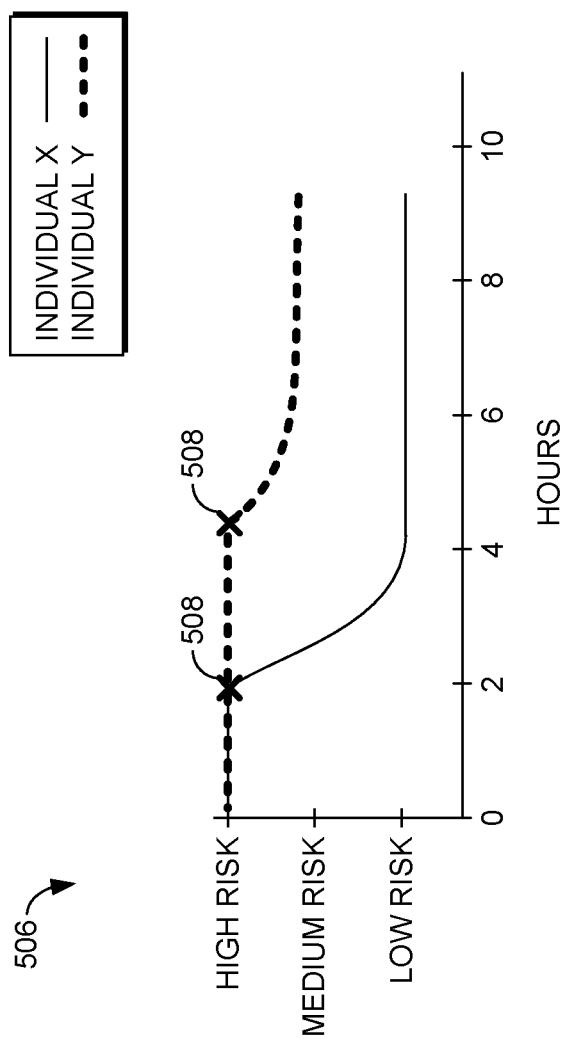

In some embodiments, the model assessment service 240 may generate graphical representations of the trends in monitoring values. FIGS. 5A-5C depict example graphical illustrations that may be generated. The graph 502 in FIG. 5A, for instance, shows performance for a predictive model on an individual level by showing the trends in monitoring values for two patients over time. Monitoring values for patient A generally have a positive trend, or a decrease in risk levels, over time, while patient B initially experienced a positive trend but later experienced a negative trend as the risk levels increased. FIG. 5B provides a graph 504 showing the population performance across multiple models. For instance, the population could include every patient being monitored with predictive models in a particular clinical facility or system of facilities. Each line shows a trend for a particular predictive model.

FIG. 5C depicts trends in risk levels for individuals based on the time of an action taken. Specifically, the graph 506 shows individual X and individual Y who both initially have high risk levels. The graph 506 shows an indicator 508 of when an action was taken for each individual. In this example, the action was taken for individual X two hours after computing a high risk level, and individual X experienced a positive trend to low risk within the following two hours. The action for individual Y, however, was taken four hours after the initial computation, and individual Y experienced a positive trend only down to medium risk within the following two hours after the action. Accordingly, graph 506 may indicate that the action taken is more effective when taken within two hours compared to when taken within four hours.

Other graphical representations not depicted may show trends in risk levels over time for different predictive models monitoring different medical conditions for the same patient and trends in risk levels over time for different populations (e.g., populations based on age, gender, medical facility, etc.) being monitored using the same predictive model.

Figure 6:
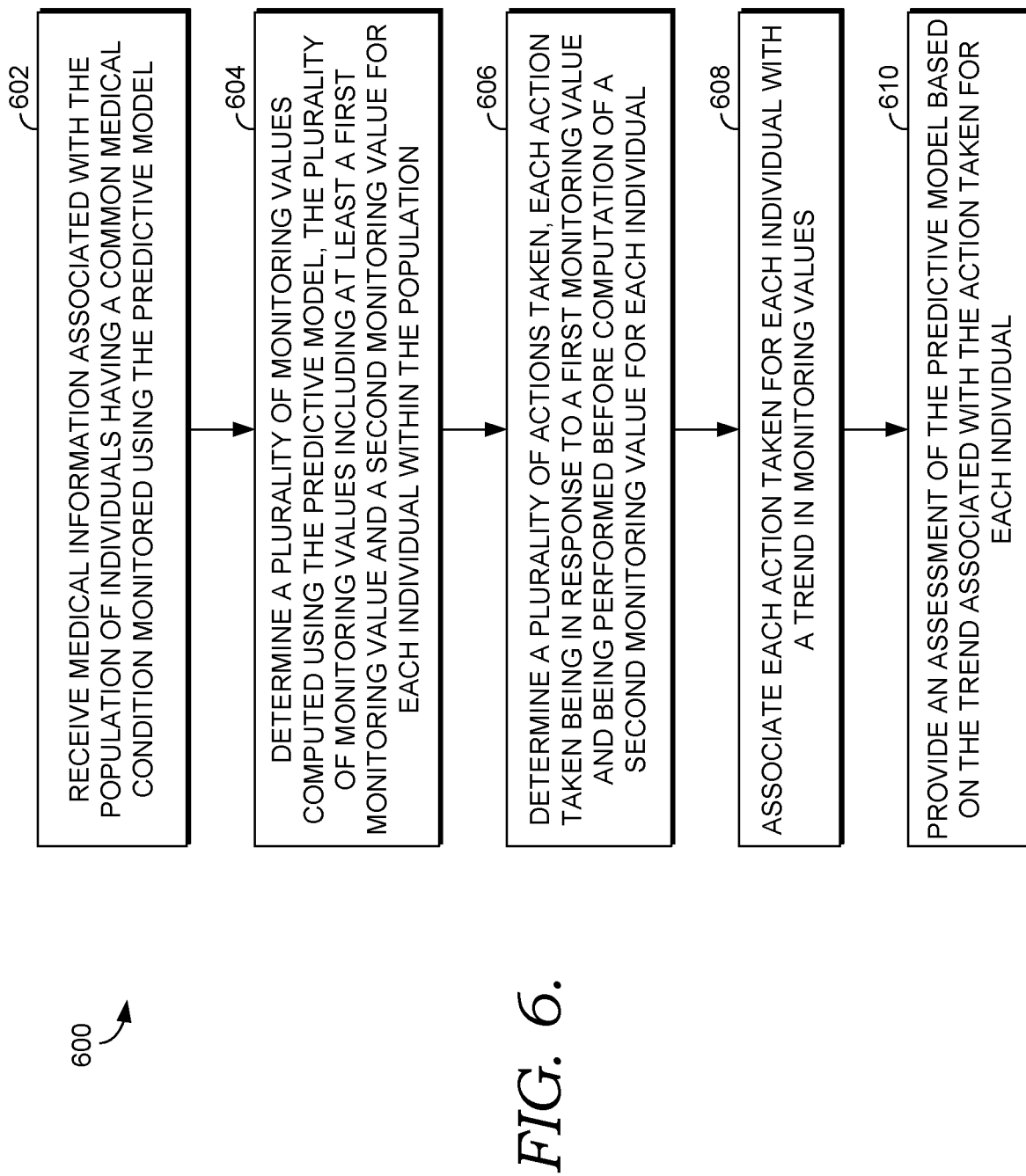
FIG. 6 is a block diagram illustrating a method for assessing the performance of the predictive model over a population of individuals in accordance with embodiments of the present invention.

Referring next to FIG. 6, a block diagram illustrating a method 600 for assessing the performance of one or more predictive models used for monitoring medical conditions of a population of individuals in accordance with embodiments of the present disclosure is provided. Each block of the method 600 and any other methods described herein comprises a computing process that may be performed using any combination of hardware, firmware, and/or software. For instance, various functions may be carried out by a processor executing instructions stored in memory. Method 600 may also be embodied as computer-usable instructions stored on computer storage media. Method 600 may be provided by a standalone application, a service or hosted service (standalone or in combination with another hosted service), or a plug-in to another product, to name a few. Method 600 may be performed at least in part, for instance, by model assessment service 240 server of FIG. 2.

As shown at step 602, method 600 includes receiving medical information, also referred to herein as clinical information, for a population of individuals. The individuals may have at least one common medical condition being monitored using a predictive model. The medical information may be received from electronic medical records associated with the individuals or a separate data store for data.

Method 600 may further comprise determining a plurality of monitoring values for individuals in the population computed using the predictive model, at step 604. The plurality of monitoring values may be determined by extracting the information from the medical information received at step 602. The plurality of monitoring values may include a series of monitoring values computed over time for each individual within the population using the predictive model. Specifically, the plurality of monitoring values may include, for each individual, at least a first monitoring value and at least a second monitoring value computed at some time after the first monitoring value. At step 606, a plurality of actions taken in response to at least some of the monitoring values are determined. Each action may have been taken in response to a first monitoring value for each individual before the second monitoring value was computed for the individual.

Method 600 may also comprise associating each action taken with a trend in monitoring values, as shown at step 608. Trends in monitoring values may include a type of trend, such as a positive trend, a negative, or a neutral trend. In some embodiment, trends further include a magnitude. For example, a first monitoring value of high risk and a second monitoring value of low risk is a positive trend but may be more specifically expressed as a positive trend by one degree or a positive trend from high to low risk. Each discovered trend is associated with at least one action taken. The action taken associated with the trend may be an action taken between the times the monitoring values on which the trend is based are computed. For instance, in response to an individual having a monitoring value of "high" risk, a medication may have been ordered, and a subsequent monitoring value of "medium" risk may have been computed for the individual. The positive trend of moving from high risk to medium risk may be associated with the action of ordering a medication.

In some embodiments, method 600 further comprises associating additional information relating to the action with the trend. Such additional information may include, for example, a recommended action provided based on the first monitoring value or a time period between the first monitoring value and the action taken in response to that first monitoring value. Additional information that may be associated with a trend also includes demographic information about the individual, the individual's medical history, and/or information about the medical facility or department in which the individual was being monitored.

Using the trends and associated actions, an assessment of the predictive model's performance may be provided, at step 610. Providing an assessment of the predictive model's performance includes analyzing the trends and associated actions and other available information to determine, among other things, whether use of the predictive models is leading to improvement of the medical conditions in the population of individuals. Frequencies with which the medical condition for individuals improves, worsens, or remains stable may be determined by aggregating the associations between trends and actions for each individual having a common medical condition being monitored by the same predictive model. These frequencies may be further based on the particular action given and/or whether the action taken was the recommended action. In some embodiments, providing an assessment of the predictive model further includes considering time periods associated with the trends. For example, the time between a first monitoring value for an individual being computed and the corresponding action being taken may be determined to have an effect on the trend in monitoring values such that a particular action may be more effective when performed within a certain amount of time.

In some embodiment, the method 600 includes determining a typical trajectory for the common medical condition based on the trends and associated actions. A typical trajectory, for example, may be a typical treatment course (i.e., actions) and typical resulting trends for individuals being monitored by the predictive model. The typical trajectory may be used as a guideline in assessing the treatment of a target individual also being monitored by the predictive model. For example, if the same actions are being taken for the target individual as in the typical trajectory but the target individual is not experiencing the same trends, a divergence may be detected between the target individual and the typical trajectory. A clinician or medical professional may then be alerted of the divergence, which may provide an opportunity to reassess the proper course of action for the target individual.

Figure 7:
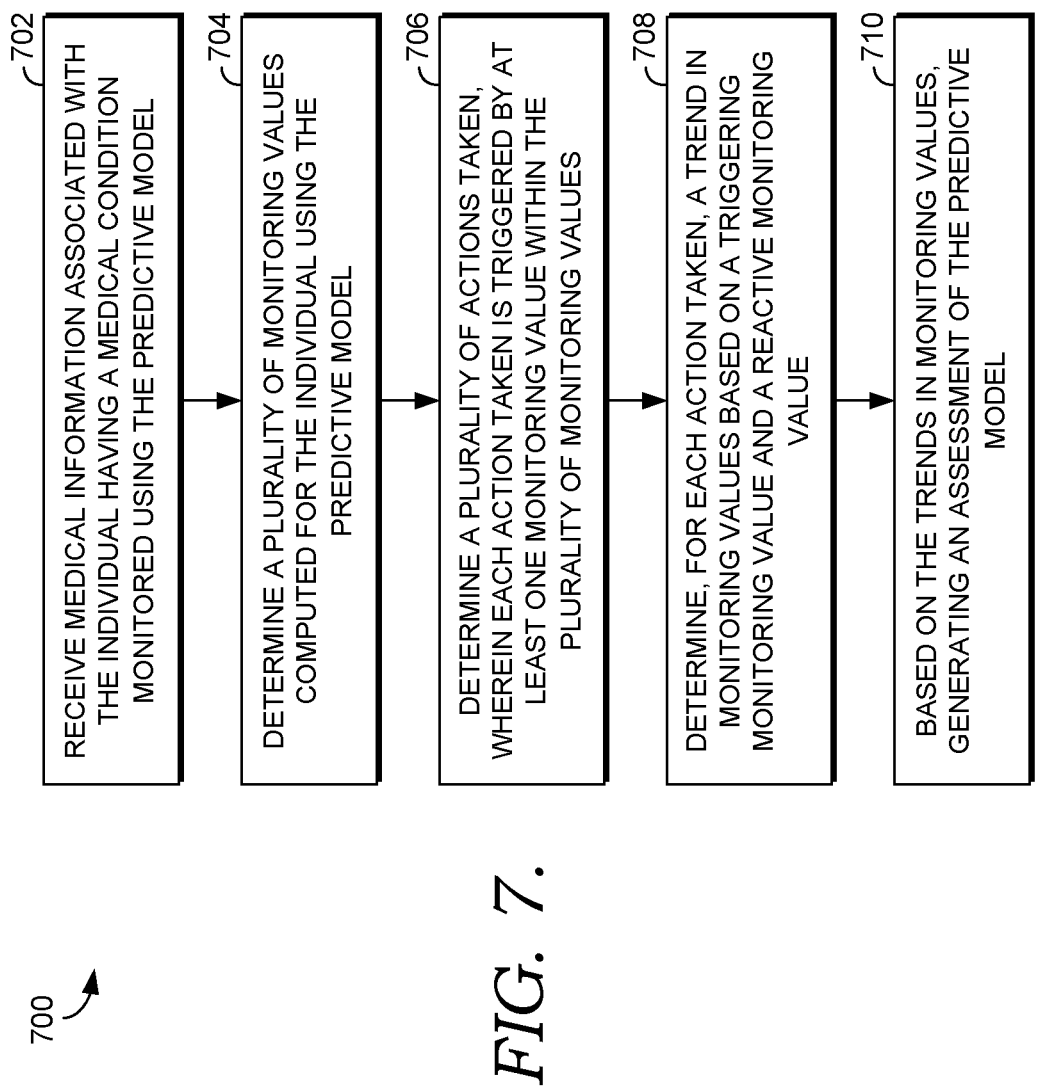
FIG. 7 is a block diagram illustrating a method for assessing the performance of the predictive model for an individual in accordance with embodiments of the present invention.

In accordance with another embodiment of the present disclosure, FIG. 7 provides a block diagram of a method 700 of assessing the performance of a predictive model for an individual. Method 700 is similar to method 600 except that is for monitoring performance on an individual level, rather than a population of individuals. Accordingly, method 700 may be performed by one or more components of the system depicted in FIG. 2, including the model assessment service 240.

At step 702, medical information associated with the individual is received. The information may be received from the individual's EMR, and the individual may have a medical condition being monitored by a predictive model. At step 704, a plurality of monitoring values computing for the individual using the predictive model is determined. Similarly, a plurality of actions taken for the individual may be determined at step 706. Each action determined may have been triggered by one of the monitoring values computed for the individual.

At step 708, a trend in monitoring values is determined for each action taken. Each trend, which may be positive, negative or neutral, is determined based on a triggering monitoring value and a reactive monitoring value. A triggering monitoring value is the monitoring value computing by the predictive model that triggers the action taken, and the reactive monitoring value is computed by the predictive model at a point in time after action is taken.

Based on the trends in monitoring values, an assessment of the predictive model is generated at step 710. The assessment may indicate whether the occurrence of the medical condition for the individual improved with the use of the predictive model. The assessment of the predictive model may indicate the frequency of the medical condition improving when the action taken was a recommended action and/or may indicate the frequency of the medical condition worsening when the action taken was not a recommended action. In some embodiment, method 700 further includes providing graphical illustrations of the performance of the predictive model for the particular individual and comparing the performance for that individual with the performance for other individuals being monitored using the same predictive model.

In addition to assessing the performance of a predictive model, embodiments of the disclosed may also assess a medical professional or healthcare provider's performance in utilizing predictive model in a care decision process. For instance, clinicians and other medical professionals may be presented with a recommended action suggested by the predictive model and have the choice of proceeding with taking the recommending action or taking an alternative action. It may be valuable to understand how often the medical professional follows the recommended action versus taking an alternative one and determine how the trends associated with actions taken that are the recommended actions compare to the trends associated with alternative actions taken.

Accordingly, embodiments may include methods and computer-readable storage devices and systems for executing methods for assessing the performance of one or more medical professional's utilization of a predictive model. Such a method may include receiving medical information from a set of electronic medical records associated with a population of individuals being treated by a medical professional using one or more predictive models. The one or more predictive models may each be monitoring a medical condition associated with individuals within the population. From the medical information, a plurality of monitoring values computed using one or more predictive models may be determined. The plurality of monitoring values may include at least a first monitoring value and a second monitoring value for each individual within the population. Additionally, a plurality of actions taken may be determined from the medical information. Each action taken within the plurality of actions may be in response to the first monitoring value and performed before computation of the second monitoring value for each individual. Next, it may be determined whether each action taken was a recommended action suggested by the one or more predictive models or was an alternative action. In some embodiments, the alternative action may include ignoring or suppressing the recommended action. For each action taken for each individual, the action taken may be associated with a trend in monitoring values. The trend in monitoring values may be based on at least the first monitoring value and the second monitoring value for each individual.

Using the trends associated with the actions taken for each individual, an assessment of the medical professional's use of the one or more predictive models may be provided. This assessment may include determining a frequency with which the action taken is a recommended action and a frequency with which the action taken is an alternative action. Further, the assessment may include determining whether actions taken that are recommended actions tend to be associated more frequently with positive trends or negative trends and, similarly, whether actions taken that are alternative actions tend to be associated more frequently with positive trends or negative trends.

These assessments may provide insight on the value of the predictive models, such as, for example, whether they are being utilized, and on whether the recommended actions suggested by the predictive models should be adjusted. Additionally, the assessments may be used by the medical professional and/or health care facility associated with the medical professional to assess the medical professional's use of the predictive model. For example, the assessment may indicate that the trends associated with actions taken by the medical professional that are alternative actions are frequently negative trends and that the trends associated with actions taken that are recommended actions are frequently positive trends. Such an assessment may be indicate that the medical professional should follow the recommended actions more often. Further, some embodiments may be provide an assessment of multiple medical professionals utilizing one or more predictive models in a similar manner as the above-recited steps. In some aspects, the assessment of multiple medical professionals may be performed based on the medical professionals' use of the same predictive model, but it is also contemplated that such an assessment may be generated for medical professionals using different predictive models.

Many different arrangements of the various components depicted, as well as components not shown, are possible without departing from the scope of the claims below. Embodiments of the disclosure have been described with the intent to be illustrative rather than restrictive. Alternative embodiments will become apparent to readers of this disclosure after and because of reading it. Alternative means of implementing the aforementioned can be completed without departing from the scope of the claims below. Certain features and sub-combinations are of utility and may be employed without reference to other features and sub-combinations and are contemplated within the scope of the claims.

What is claimed is:

1. One or more computer-readable storage devices having computer-executable instructions embodied thereon that, when executed, facilitate a method for assessing performance of a predictive model on a population of individuals, the method comprising:
   receiving medical information from a set of electronic medical records associated with the population of individuals having a common medical condition monitored using the predictive model;
   determining, from the medical information, a plurality of monitoring values computed using the predictive model, the plurality of monitoring values including at least a first monitoring value and a second monitoring value for each individual within the population;
   determining, from the medical information, a plurality of actions taken, each action taken within the plurality of actions taken being in response to the first monitoring value and being performed before computation of the second monitoring value for each individual, each action taken corresponding to a recommended action generated by the predictive model in response to the first monitoring value wherein the recommended action is generated prior to a first discharge of the individual from a healthcare facility;
   determining a plurality of time periods, wherein each time period within the plurality of time periods is an amount of time between a time the recommended action is provided and the action being taken, wherein each time period occurs prior to the first discharge;
   associating each action taken for each individual with a trend in monitoring values and the amount of time between the time the recommended action is provided and the action taken, the trend being based on at least the first monitoring value and the second monitoring value for each individual;
   generating an assessment of the predictive model based on the trend associated with the action taken for each individual and the amount of time, the assessment of the predictive model indicating at least whether occurrence of the common medical condition within the population of individuals improved with use of the predictive model and indicating whether one or more time periods within the plurality of time periods is more likely than other time periods to improve occurrence of the common medical condition within the population of individuals; and
   adjusting the predictive model based on the generated assessment.

2. The computer-readable storage devices of claim 1, wherein the plurality of actions taken includes one or more of the following: prescribing a drug, ordering a procedure or set of procedures, assigning a medical care coach, and an inaction.

3. The computer-readable storage devices of claim 2, wherein the inaction comprises suppressing or disregarding a recommended action suggested by the predictive model.

4. The computer-readable storage devices of claim 1, wherein each of the plurality of monitoring values indicate one of the following risk levels associated with the common medical condition: high risk, medium risk, and low risk.

5. The computer-readable storage devices of claim 4, wherein the trend in monitoring values for each individual is one of the following: a positive trend indicating a decrease in risk, a negative trend indicating an increase in risk, and a neutral trend indicating no change in risk.

6. The computer-readable storage devices of claim 1, wherein the method further comprises determining a plurality of recommended actions, each recommended action being suggested by the predictive model in response to the first monitoring value for each individual.

7. The computer-readable storage devices of claim 6, wherein providing the assessment of the predictive model includes determining a frequency with which an action taken within the plurality of actions taken was the recommended action suggested by the predictive model.

8. The computer-readable storage devices of claim 7, wherein providing an assessment of the predictive model further includes determining a frequency of positive trends indicating improvement of the common medical condition when the action taken was the recommended action.

9. The computer-readable storage devices of claim 7, wherein the method further includes identifying a medical professional associated with each action taken, wherein providing an assessment of the predictive model further includes determining, for each medical professional identified, a frequency with which the action taken by the medical professional is a recommended action and a frequency with which the action taken by the medical professional is an alternative action.

10. A computerized method for assessing performance of a predictive model on an individual:
   receiving medical information from a set of electronic medical records associated with the individual having a medical condition monitored using the predictive model;
   determining a plurality of monitoring values computed for the individual using the predictive model;
   determining a plurality of actions taken for the individual, wherein each action taken is triggered by at least one monitoring value within the plurality of monitoring values;
   determining, for each action taken, a trend in monitoring values based on a triggering monitoring value and a reactive monitoring value, wherein the triggering monitoring value triggered the action taken and the reactive monitoring value was computed after the action taken, each action taken corresponding to a recommended action by the predictive model in response to the first monitoring value, wherein the recommended action is generated prior to a first discharge of the individual from a healthcare facility;
   associating the action taken for each individual with the trend in monitoring values;

determining a plurality of time periods, wherein each time period within the plurality of time periods is an amount of time between the a time the recommended action is provided and the action being taken, wherein each time period occurs prior to the first discharge;

based on at least the trends in monitoring values and the amount of time, generating an assessment of the predictive model, wherein the assessment indicates whether occurrence of the medical condition for the individual improves with use of the predictive model and indicates whether one or more time periods within the plurality of time periods is more likely than other time periods to improve occurrence of the medical condition; and adjusting the predictive model based on the generated assessment.

11. The computerized method of claim 10, wherein each trend in monitoring values comprises one of the following: a positive trend indicating an improvement in the medical condition, a negative trend indicating a worsening of the medical condition, and a neutral trend indicating no change in the medical condition.

12. The computerized method of claim 10 further comprising determining a plurality of recommended actions suggested by the predictive model, each recommended action being suggested in response to the triggering monitoring value.

13. The computerized method of claim 12, wherein one or more of the actions taken within the plurality of actions taken comprises one of the recommended actions.

14. The computerized method of claim 13, wherein the assessment of the predictive model indicates whether occurrence of the medical condition for the individual improves when the action taken comprises one of the recommended actions.

15. One or more computer-readable storage devices having computer-executable instructions embodied thereon that, when executed, facilitate a method for assessing performance of a predictive model, the method comprising:

receiving medical information from a set of electronic medical records associated with a population of individuals having a common medical condition monitored using the predictive model;

determining, for each individual within the population, a first monitoring value computed using the predictive model;

determining, for each first monitoring value, a recommended action suggested by the predictive model in response to the first monitoring, wherein the recommended action is generated prior to a first discharge of the individual from a healthcare facility;

determining, for each first monitoring value, an action taken in response to the first monitoring value;

determining, for each individual within the population, a second monitoring value computed using the predictive model after performance of the action taken in response to the first monitoring value;

based on the first monitoring value and the second monitoring value for each individual, determining a trend in monitoring values, wherein each trend comprises a decrease in risk, an increase in risk, or no change in risk;

associating the action taken for each individual with the trend in monitoring values;

determining a plurality of time periods, wherein each time period within the plurality of time periods is an amount of time between a time the recommended action is provided and the action being taken, wherein each time period occurs prior to the first discharge;

based on the trend in monitoring values for each individual and the amount of time, generating one or more assessments for the predictive model, wherein the one or more assessments indicate at least whether the common medical condition in individuals within the population tends to improve when the action taken is the recommended action suggested by the predictive model and indicating whether one or more time periods within the plurality of time periods is more likely than other time periods to improve occurrence of the common medical condition within the population of individuals; and adjusting the predictive model based on the one or more assessments.

16. The one or more computer-readable storage devices of claim 15, wherein the action taken in response to the first monitoring value for each individual is one or more of the following: prescribing a drug, ordering a procedure or set of procedures, assigning a medical care coach, or an inaction.

17. The one or more computer-readable storage devices of claim 15, wherein the method further comprises:

discovering additional trends for each individual within the population, each trend within the additional trends being based on monitoring values computed using the predictive model; and associating each additional trend with an additional action taken in response to at least one of the monitoring values.

18. The one or more computer-readable storage devices of claim 17, the method further comprising determining a typical trajectory for the common medical condition based on at least the additional trends and additional actions taken for each individual.

19. The one or more computer-readable storage devices of claim 18, the method further comprising:

receiving a second set of medical information from electronic medical records associated with a target individual having the common medical condition, wherein the second set of medical information includes a second plurality of monitoring values computed for the target individual using the predictive model and a second plurality of actions, each action within the second plurality of actions being taken in response to at least one monitoring value within the second plurality of monitoring values;

detecting a divergence of at least one trend determined for the target individual and the typical trajectory; and notifying a medical professional of the divergence.

* * * * *

UNITED STATES PATENT AND TRADEMARK OFFICE
CERTIFICATE OF CORRECTION

| | |
|---|---|
| PATENT NO. | : 11,244,764 B2 |
| APPLICATION NO. | : 15/386906 |
| DATED | : February 8, 2022 |
| INVENTOR(S) | : Kanakasabha Kailasam et al. |

It is certified that error appears in the above-identified patent and that said Letters Patent is hereby corrected as shown below:

In the Specification

In Column 4, Line 15, Delete "Electronic" and insert -- Electronics --.

In the Claims

In Column 17, Line 3, Claim 10, delete "the a" and insert -- a --.

Signed and Sealed this
Third Day of May, 2022

*Katherine Kelly Vidal*

Katherine Kelly Vidal
*Director of the United States Patent and Trademark Office*